United States Patent
Dahlberg (10) Patent No.: US 8,239,026 B2
(45) Date of Patent: Aug. 7, 2012

(54) IMPLANTABLE MEDICAL DEVICE WITH A VOLTAGE PROTECTION CIRCUIT

(75) Inventor: Kenneth Dahlberg, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 740 days.

(21) Appl. No.: 12/065,106

(22) PCT Filed: Sep. 28, 2005

(86) PCT No.: PCT/SE2005/001440
§ 371 (c)(1),
(2), (4) Date: Feb. 28, 2008

(87) PCT Pub. No.: WO2007/037727
PCT Pub. Date: Apr. 5, 2007

(65) Prior Publication Data
US 2008/0228270 A1  Sep. 18, 2008

(51) Int. Cl.
*A61N 1/00* (2006.01)
(52) U.S. Cl. ........................................... 607/37; 607/36
(58) Field of Classification Search ............... 607/36–37
See application file for complete search history.

(56) References Cited

U.S. PATENT DOCUMENTS

| | | | |
|---|---|---|---|
| 4,329,733 A | 5/1982 | Ito et al. | |
| 5,333,095 A * | 7/1994 | Stevenson et al. | 361/302 |
| 5,905,627 A * | 5/1999 | Brendel et al. | 361/302 |
| 6,505,072 B1 * | 1/2003 | Linder et al. | 607/32 |
| 6,614,406 B2 | 9/2003 | Amundson et al. | |
| 2003/0135246 A1 | 7/2003 | Mass et al. | |
| 2004/0176811 A1 * | 9/2004 | Von Arx et al. | 607/32 |

FOREIGN PATENT DOCUMENTS

| | | |
|---|---|---|
| EP | 0 623 363 | 11/1994 |
| EP | 0 916 364 | 5/1999 |
| EP | 1 400 993 | 3/2004 |
| WO | WO 2006/057587 | 6/2006 |

* cited by examiner

*Primary Examiner* — Nicole F Lavert (57) ABSTRACT

An implantable medical device has a hermetically sealed housing with at least one feedthrough therein for a conductive path between an RF antenna carried by the housing, and an RF telemetry circuit contained in the housing. The feedthrough has a feedthrough housing with a capacitor element therein having first and second capacitor plate configurations, with a first of the capacitor plate configurations being connected to the RF antenna and a second of the capacitor plate configurations being connected to the RF telemetry circuit. The feedthrough functions both as a hermetic seal and as a galvanic isolation for voltage protection of the components of the RF telemetry circuit, and other circuitry in the sealed housing connected thereto.

11 Claims, 10 Drawing Sheets

IMPLANTABLE MEDICAL DEVICE WITH A VOLTAGE PROTECTION CIRCUIT

BACKGROUND OF THE INVENTION

1. Field of the Invention

The present invention generally relates to implantable medical devices such as implantable cardiac pacemakers and implantable cardioverter/defibrillators, and in particular to a capacitive feedthrough for filtering off external interference signals, e.g. defibrillation signals, in order to protect the electronic circuits and telemetry circuits of such an implanted device.

2. Description of the Prior Art

Implantable medical devices, including cardiac rhythm management devices such as pacemakers and implantable cardioverter/defibrillators, typically have the capability to communicate data with an external programmer via a radiofrequency telemetry link. A clinician may use such an external programmer to program the operating parameters of an implanted medical device. For example, the pacing and other operating characteristics of a pacemaker are typically modified after implantation in this manner. Modern implantable devices also include the capability for bidirectional communication so that information can be transmitted to the programmer from the implanted device. Among the data which may typically be telemetered from an implantable device are various operating parameters and physiological data. The implantable device generates and receives the radio signals by means of an antenna. Today, antennas capable of far-field communications are of increasing interest in implantable medical devices, which allows communication over much greater distances than inductively coupled antennas.

The technology of cardiac pacemakers has developed in sophistication and functionality over the years. In general, cardiac pacemakers are designed to control the heart by correcting or compensating for various heart abnormalities which can be encountered in human patients. For example, cardiac pacemakers may provide therapeutic stimulation to the heart by delivering therapeutic pulses such as pacing, cardioversion or defibrillation pulses. However, with this increasing sophistication has come a concomitant increase in sensitivity of the implantable devices to misoperation due to external influences such as defibrillation, electrocautery, and the like. Such interference or voltage pulses may be received by the antenna, for example, at locations where galvanic exposure against tissue occurs and may be conducted further into the electronic circuits and RF telemetry circuits of the medical device. This may cause the medical device to falsely identify the interference as being of cardiac origin and give rise to, for example, an erroneous output rate, or in worst case, it may change the state of or destroy components of the circuits, which, in turn, may severely damage the functions of the medical device.

Conventional implantable devices, such as cardiac pacemakers and implantable cardioverter/defibrillators, are therefore generally provided with protection circuits or filter circuits adapted to protect the electronic circuits and RF telemetry circuits of the medical device against undesired voltage pulses, i.e. to filter off external voltage transients or pulses. Conventionally, a capacitance is arranged within the device and connected in series with the antenna and the electronic circuits and RF telemetry circuits as protection circuit or filter circuit adapted to filter off external interference signals such as defibrillation signals. Thus, RF signals are transferred via the antenna lead through the galvanically conductive feedthrough passing through the serial capacitor while external interference signals are filtered off.

However, this conventional solution is impaired with a number of drawbacks. For example, the filter circuit, i.e. the capacitor, requires extra space, which may be a problem in implantable devices, such as cardiac pacemakers, where internal space is limited. Moreover, since the external interference signals are transferred into the hermetically sealed device, they may give rise to interference leakage within the device.

Hence, there is a need for an improved circuit that in an effective way can protect the internal circuits of an implanted medical device against undesired voltage pulses caused by exposure to e.g. defibrillation and/or electrocautery.

SUMMARY OF THE INVENTION

Thus, an object of the present invention is to provide an improved protection circuit that can effectively protect the internal circuits of an implanted medical device against undesired voltage pulses caused by exposure to defibrillation and/or electrocautery received by the antenna, for example, at galvanic exposure against tissue and be conducted further into the electronic circuits and RF telemetry circuits of the medical device.

Another object of the present invention is to provide such a protection circuit that can be implemented in an implanted medical device in a space efficient manner.

A further object of the present invention is to provide such a protection circuit that can be implemented in an implanted medical device in a cost efficient manner.

According to an aspect of the present invention, there is provided an implantable medical device including a hermetically sealed housing having at least one feedthrough arranged for at least one RF telemetry antenna. The medical device has at least one RF telemetry circuit having an RF transmitter and receiver connected to the antenna; at least one controller circuit adapted to output and receive data contained in a modulated carrier generated or received, via the antenna, by the RF telemetry circuitry; wherein the feedthrough has a feedthrough housing and a capacitor element arranged in the feedthrough housing, the element being connected in series between the RF telemetry circuit and the antenna and including at least one first capacitor plate being connected to the antenna and at least one second capacitor plate being connected to the RF telemetry circuit, the capacitor element being adapted to withstand the voltage amplitude of a pulse capable of modifying state of or destroying at least one component of the RF telemetry circuit or the electronic circuit.

Thus, the invention is based on the idea of arranging the feedthrough for the antenna as a filter circuit serving the dual purposes of functioning as a hermetic seal and a galvanic insulation circuit for blocking voltage transients or pulses, due to exposure to defibrillation and/or electrocautery conducted into the device due to galvanic contact between the RF circuits of the device and tissue via an antenna external to the housing in tissue contact and capable of modifying state of or destroying at least one component of the RF telemetry circuit or the electronic circuit, from reaching the components. Accordingly, the need of a separate galvanically conducting feedthrough is removed.

This solution provides several advantages over the conventional technique. One advantage is that, since the filter circuit, i.e. the capacitor element, is integrated in the antenna feedthrough, valuable space in the medical device can be saved. Another advantage is that the risk of possible interference leakage into the hermetically sealed device can be significantly reduced due to the fact that the filter circuit, i.e. the capacitor, is arranged in the feedthrough and, thus, prevents the external voltage transients or pulses from entering into the medical device. Furthermore, combining two functions, i.e. the hermetic seal and the galvanic isolation, in the feedthrough entails cost savings, which also is an advantage in comparison with the known technique.

Preferably, the at least one first capacitor plate is facing outwards from the device and is being made of a bio compatible material, for example, titanium, platinum, or alumina.

In a further embodiment of the present invention, the at least one first capacitor plate comprises a first set of capacitor plates being interconnected to each other and the at least one second capacitor plate comprises a second set of capacitor plates being interconnected to each, wherein plates from the first set are alternated with plates from the second set and adjacent plates are separated with an isolating dielectric material.

In an embodiment of the present invention, the feedthrough housing has a substantially cylindrical shape and the plates of the first set of capacitor plates and the second set of capacitor plates are substantially circular and are arranged substantially coaxially in the feedthrough housing. According to this embodiment, the plates of the first and second set of capacitor plates are arranged substantially parallel with each other and thus forming a pile- or stack-like configuration.

In a further embodiment of the present invention, intermediate plates of the first set of capacitor plates and intermediate plates of the second set of capacitor plates are provided with via holes, the first set of intermediate capacitor plates being coupled to each other by means of leads arranged through the via holes of the plates of the second set, and the second set of intermediate capacitor plates being coupled to each other by means of leads arranged through the via holes of the plates of the first set.

In accordance with yet another embodiment of the present invention, a first connecting element is connected to the antenna and a second connecting element is connected to the RF telemetry circuit, wherein the plates of the first and second set of capacitor plates are connected to the first connecting element and to the second connecting element, respectively, and wherein the plates of the first and second set of capacitor plates are arranged substantially perpendicular to the first and second connecting element, respectively.

Preferably, the feedthrough housing has a substantially cylindrical shape and the capacitor plates of the first set of intermediate capacitor plates and the second set of intermediate capacitor plates are substantially rectangular, each plate having a width being substantially equal to an inner width of a longitudinal cross-section of the substantially cylindrically shaped feedthrough housing. Accordingly, the widths of adjacent plates will vary depending on the inner width of the feedthrough housing at the specific location of the plate.

In still another embodiment of the present invention, the plates of first and second set of intermediate capacitor plates are arranged as substantially concentric cylinders.

According to an embodiment of the present invention, the capacitor element is adapted to function as an antenna matching element.

Conveniently, the capacitor element according to the present invention is dimensioned to withstand a voltage exceeding 100 V.

BRIEF DESCRIPTION OF THE DRAWINGS

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

DESCRIPTION OF THE PREFERRED EMBODIMENTS

Figure 1:
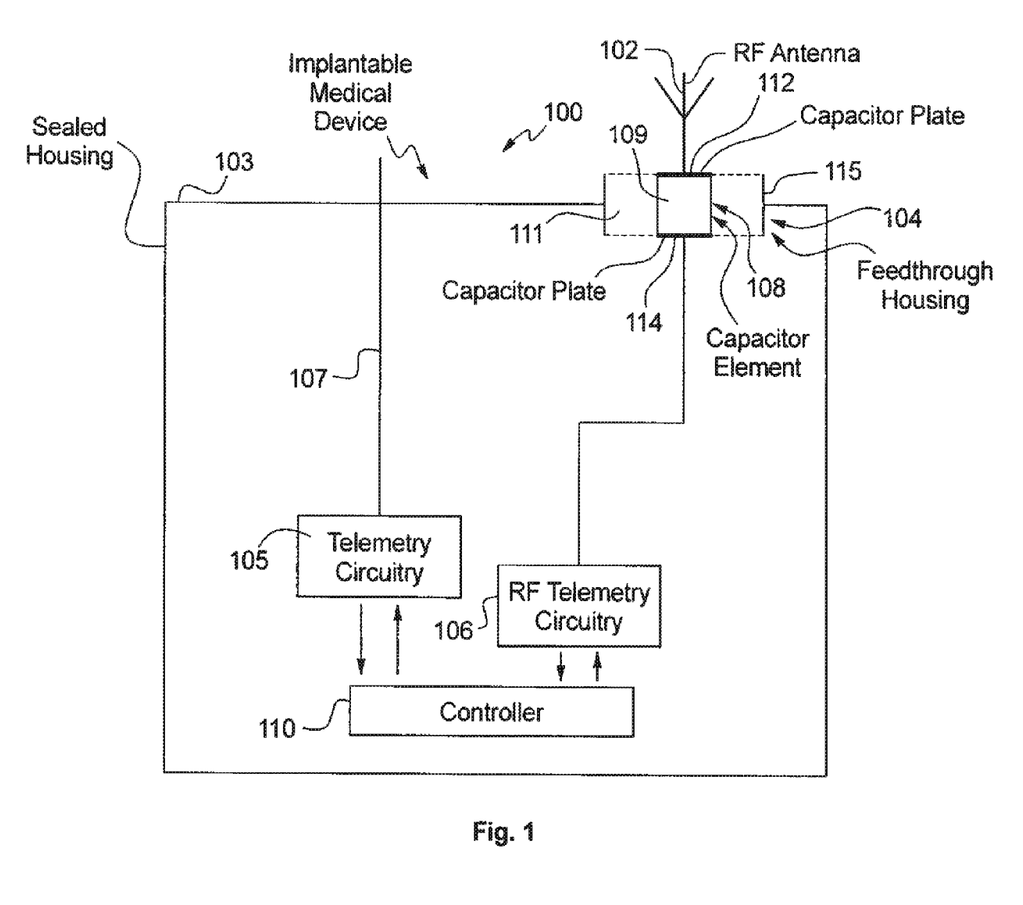
FIG. 1 diagrammatically shows an implantable medical device comprising a capacitive feedthrough for protecting the electronic circuitry of the device against undesired voltage pulses caused by exposure to defibrillation and/or electrocautery conducted into the device due to galvanic contact between the RF circuits of the device and tissue via an antenna or apart of the medical device capable of functioning as an antenna being in tissue contact and connected to electronic circuitry of the device in accordance with the general principles of the present invention.

With reference first to FIG. 1, an implantable medical device (IMD) 100 having a serial capacitive feedthrough adapted to protect the electronic circuitry of the device against undesired voltage transients caused by exposure to defibrillation and/or electrocautery conducted into the device via an antenna or a part of the medical device capable of functioning as an antenna being in tissue contact and connected to electronic circuitry of the device in accordance with the present invention will be described.

The IMD 100 is provided with an antenna 102 for communication with external devices such as an external programmer. Preferably, the antenna 102 is suitable for radiating and receiving far-field electromagnetic radiation. It should be noted that the housing effectively is a part of the antenna and affects the radiation properties of the antenna 102. The housing is further in contact with the tissue. The IMD 100 includes a hermetically sealed housing 103 provided with an antenna feedthrough 104 through which the antenna 102 is located and feedthroughs for medical leads, which housing 103 typically is formed of a biocompatible metal, e.g. titanium. The housing 103 contains a therapy circuitry 105 for providing particular functionality to the device such as cardiac rhythm management, or neuromuscular stimulation, RF telemetry circuitry 106 for providing RF communications. A battery (not shown) supplies power to the electronic circuitry within the housing 103. One or more leads 107 are connected to the therapy circuitry 105, which lead or leads 107 may be unipolar or bipolar, and may be adapted to operate in cooperation with a wide variety of implantable medical devices. Moreover, the lead or the leads 107 may include any of the passive or active fixation mechanisms known in the art for fixation of the lead 107 to the cardiac tissue when final position has been found. As an example, lead distal tip (not shown) may include a tined tip or a fixation helix. The leads 107 also carry one or more electrodes, such as a tip electrode or a ring electrode. The electrode senses electrical signals associated with depolarization and repolarization of the heart. In addition, the electrode may also transmit pacing pulses for causing depolarization of cardiac tissue adjacent to the electrode. Furthermore, the leads 107 also comprise sensing means arranged to sense signals related heart activity.

A microprocessor controller 110 controls the operation of the therapy circuit 105, which includes sensing and stimulus generation circuitry that are connected to the electrodes of the lead or leads 107 for control of heart rhythm, and the RF telemetry circuitry for transmitting and receiving a carrier signal at a specific frequency modulated with telemetry data.

The controller 110 also outputs and receives the data contained in the modulated carrier generated or received by the RF telemetry circuitry 106. The RF telemetry circuitry 106 comprises an RF transmitter and receiver that are connected to the antenna 102.

The capacitive feedthrough includes an antenna feedthrough housing 104 and a capacitor element 108 connected in series with the antenna 102 and is arranged to withstand a voltage amplitude of a pulse received by the antenna 102 and capable of modifying the state of or destroying components of the RF telemetry circuitry 106, the controller 110, or the therapy circuit 105. Preferably, the capacitor element is dimensioned to withstand a voltage exceeding 100 V, and, more preferably, to withstand a voltage in the range of 75-1000 V.

The capacitor element 108 can also be adapted to function as a matching circuit to adjust the impedance of the antenna 102 to the impedance of the RF telemetry circuitry 106. The capacitor element loads the antenna 102 with an amount of capacitance to thereby adjust the effective electrical length of the antenna, and hence the resonance frequency of the antenna. By matching the antenna impedance to the impedance of the RF telemetry circuitry at a specific carrier frequency, the reactance of the antenna may be tuned out at that frequency so that the antenna forms a resonant structure and efficiently transmits/receives far-field radiation.

According to the general principles of the present invention, the capacitor element 108 includes at least one first capacitor plate 112 and at least one second capacitor plate 114. A cavity 109 defined by the feedthrough housing 104, the at least one first capacitor plate 112 and the at least one second capacitor plate 114 is filled with an isolating dielectric material. According to embodiments of the present invention, the dielectric material is hermetic, essentially free of pores and diffusion proof in order to function as a feedthrough material. Moreover, the dielectric material is an electrically insulating material with low losses, i.e. a high Q material. Examples of such materials are COG materials, such as NPO with a high Q value. In addition, the dielectric material should have a relatively high K value, i.e. a dielectric constant high enough to achieve the desired capacitance for the utilized frequencies as the same time as the size of the capacitor is kept at an appropriate size. Typical frequencies used for signal transfer in this kind of applications, i.e. implantable medical devices such as pacemakers, are 402-405 MHz where 110-150 pF is suitable capacitance values and about 2.45 GHz where 6-12 pF is suitable capacitance values. In a case where two or more frequencies are used, a suitable capacitance value may be in the range of 15-60 pF for the above mentioned frequency ranges. Another suitable capacitance value range is 25-40 pF for the above mentioned frequency ranges. Yet another suitable capacitance value is about 33 pF. It may be advantageous, from an electrical and signal standpoint, to use a low K material in an area 111 between the capacitor element 108 and an outer cylinder 115 of the feedthrough, which cylinder may be made of metal. K is defined as the ratio of the capacitance with a volume of dielectric compared to that of a vacuum dielectric, thus, $K=\epsilon d/\epsilon 0$, where $\epsilon d$ is the permittivity of the dielectric and $\epsilon 0$ is the permittivity of free space. Thereby, the capacitive coupling between the capacitor and the housing 103 can be reduced. Such a low K material may be various mineral/ceramic material such as e.g. alumina (Al2O3), various types of glass, e.g. Pyrex or glass frit seal s or mixtures thereof, and low K alumina/glass compounds as used in LTCC ceramics for use in high frequency applications.

The first plate 112 is arranged such that on outer side of it faces outwards from the device 100. Thus, it may under certain circumstances be in tissue contact and is made of a bio-compatible material such as titanium, platinum, alumina, etc. The antenna 102 is attached to the first plate 112, and second plate 114, is connected to the RF circuit (see FIG. 1). Preferably, the capacitor element 108 is arranged such that the shunt capacitance of the capacitor is minimized.

Furthermore, as discussed above, the isolating dielectric material 109 and the first and second plates 112 and 114, respectively, of the capacitor element 108 integrated into the feedthrough housing 104, are arranged such that a hermetic seal is provided. That is, the capacitor body or capacitor element 108 functions both as a hermetic seal and as a galvanic isolation and, hence, size, cost, and possible interference leakage can be reduced.

Figure 2:
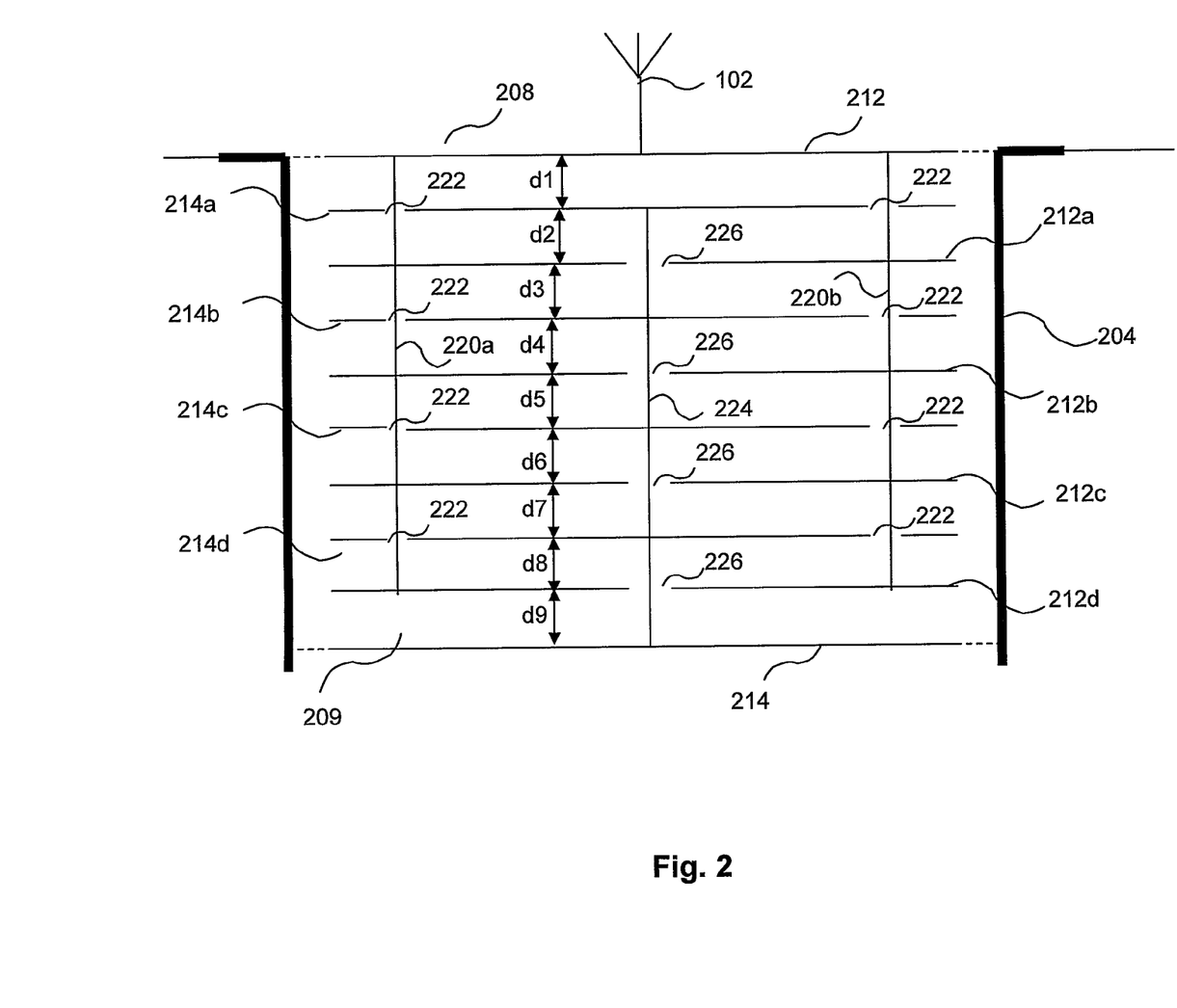
FIG. 2 diagrammatically shows a cross-sectional view of an embodiment of the feedthrough according to the present invention.
Figure 3:
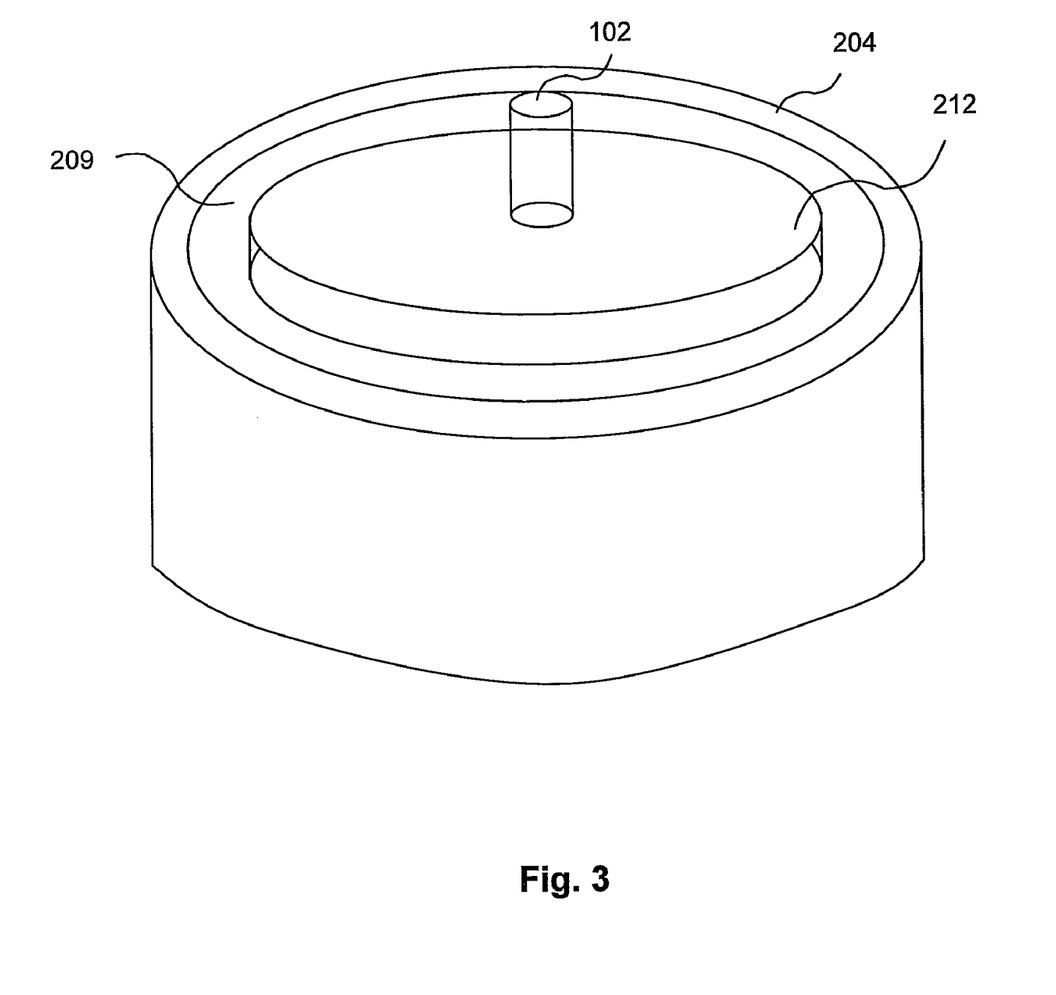
FIG. 3 is a diagrammatic perspective view of the feedthrough shown in FIG. 2.

With reference now to FIGS. 2 and 3, an embodiment of the feedtrough including a capacitor according to the present invention will be described in detail. Like or similar parts having like or similar function shown in FIGS. 1 and 2, respectively, are denoted with the same reference numerals. The feedthrough includes a capacitor element 208 and a feedthrough housing 204. As described above, the capacitor body or capacitor element 208 functions both as a hermetic seal and galvanic isolation and, hence, size, cost, and possible interference leakage can be reduced.

The antenna 102 is attached to at least one first capacitor plate 212, or anode. At least one second capacitor plate 214, or cathode, is connected to the RF circuit (not shown in FIG. 2, see FIG. 1). Preferably, the at least one first capacitor plate 212 and the at least one second capacitor plate 214 are arranged in the feedthrough housing 204 such that the feedthrough housing 204 together with the first and second plates 212 and 214, respectively, defines an inner cavity 209. In this embodiment, the feedthrough housing 204 has a circular cross-section in a plane perpendicular to the plane of the cross-section shown in FIG. 2. The first and second plate 212 and 214, respectively, have a circular shape in the plane perpendicular to the plane of the cross-section shown in FIG. 2, and, thus, a cylindrical cavity 209 is formed by the housing 204 and the first and second plates 212 and 214, respectively.

In FIG. 3, the housing 204 and the first capacitor plate 212, which also is an outer plate with respect to the casing or housing 103, are shown in a top perspective view. A lower part of the antenna 102 is also shown.

Furthermore, the first capacitor plate 212, or the first anode, is interconnected to a number of intermediate anode plates 212a-212d, which in this embodiment is four. The intermediate anode plates 212a-212d are arranged within the cavity 209. In the same manner, as illustrated, the second capacitor plate 214, or the second cathode, is interconnected to a number of intermediate cathode plates 214a-214d, which in this embodiment is four. The intermediate cathode plates 214a-214d are also arranged within the cavity 209. Of course, as the skilled man realizes, the number of intermediate plates can be varied in accordance with, for example, requirements regarding size or in order to tune the capacitance of the capacitor element 208.

Intermediate anode plates 212a-212d and intermediate cathode plates 214a-214d are arranged in an alternating manner. The intermediate plates 212a-212d, and 214a-214d are arranged such they are substantially parallel with each other, respectively. In addition, the plates 212, 214, 212a-212d, and 214a-214d are substantially circular, in the plane perpendicular to the plane of the cross-section shown in FIG. 2, and are arranged coaxially such that they form a stack-like configuration. Adjacent plates are separated with gaps d1-d9, which in this embodiment are substantially equal i.e. d1=d2=d3=d4=d5=d6=d7=d8=d9. These gaps d1-d9 may be changed in order to tune the capacitance of the capacitor element 208.

The inner cavity 209 defined by the feedthrough housing 204 and first and second plates 212 and 214, respectively, and including the intermediate plates 212a-212d and 214a-214d is filled with an isolating dielectric material in accordance with the discussion above such that the feedthrough housing 204, the capacitor plates and the isolating dielectric material forms a galvanic isolation and a hermetic seal.

The anode plates 212, 212a-212d are interconnected with each other by means of wires or leads 220a and 220b, which are arranged in via holes 222 arranged in the cathode plates 214a-214d such that the wires 220a and 220b are isolated from the plates. The cathode plates 214, 214a-214d are in a corresponding way interconnected with each other by means of a wire 224 arranged in via holes 226 in the anode plates 212a-212d. As can be seen from FIG. 2, the capacitor plates 212, 214, 212a-212d, and 214a-214d according to this embodiment have, in a plane perpendicular to the direction of the wires or leads 220a and 220b, a substantially circular shape, as mentioned above. However, as the skilled man within the art realizes, the size and shape of the feedthrough housing 204 may be another than circular, for example squarelike, rectangular or octagonal. Thus, the size and shape of the plates can also be changed, for example, the shape in the plane perpendicular to the direction of the wires or leads 220a and 220b may be substantially octagonal or square. In addition, the gaps d1-d9 between adjacent plates can vary. As an example, the gaps d1, d3, d5, d7, and d9 can be longer than the gaps d2, d4, d6, and d8, or in other words, d1=d3=d5=d7=d9>d2=d4=d6=d8.

As discussed above, the capacitor element 208 is preferably dimensioned to withstand a voltage exceeding 100 V, and, more preferably, to withstand a voltage in the range of 75-1000 V. Furthermore, the capacitor element 208 is preferably arranged such that the shunt capacitance of the capacitor is minimized.

With reference now to FIGS. 4-7, another embodiment of the feedtrough including a capacitor according to the present invention will be described in detail. Like or similar parts having like or similar function shown in FIGS. 1 and 2, respectively, are denoted with the same reference numerals. The feedthrough includes a capacitor element 308 and a feedthrough housing 304. As described above, the capacitor body or capacitor element 308 functions both as a hermetic seal and galvanic isolation and, hence, size, cost, and possible interference leakage can be reduced.

Figure 4:
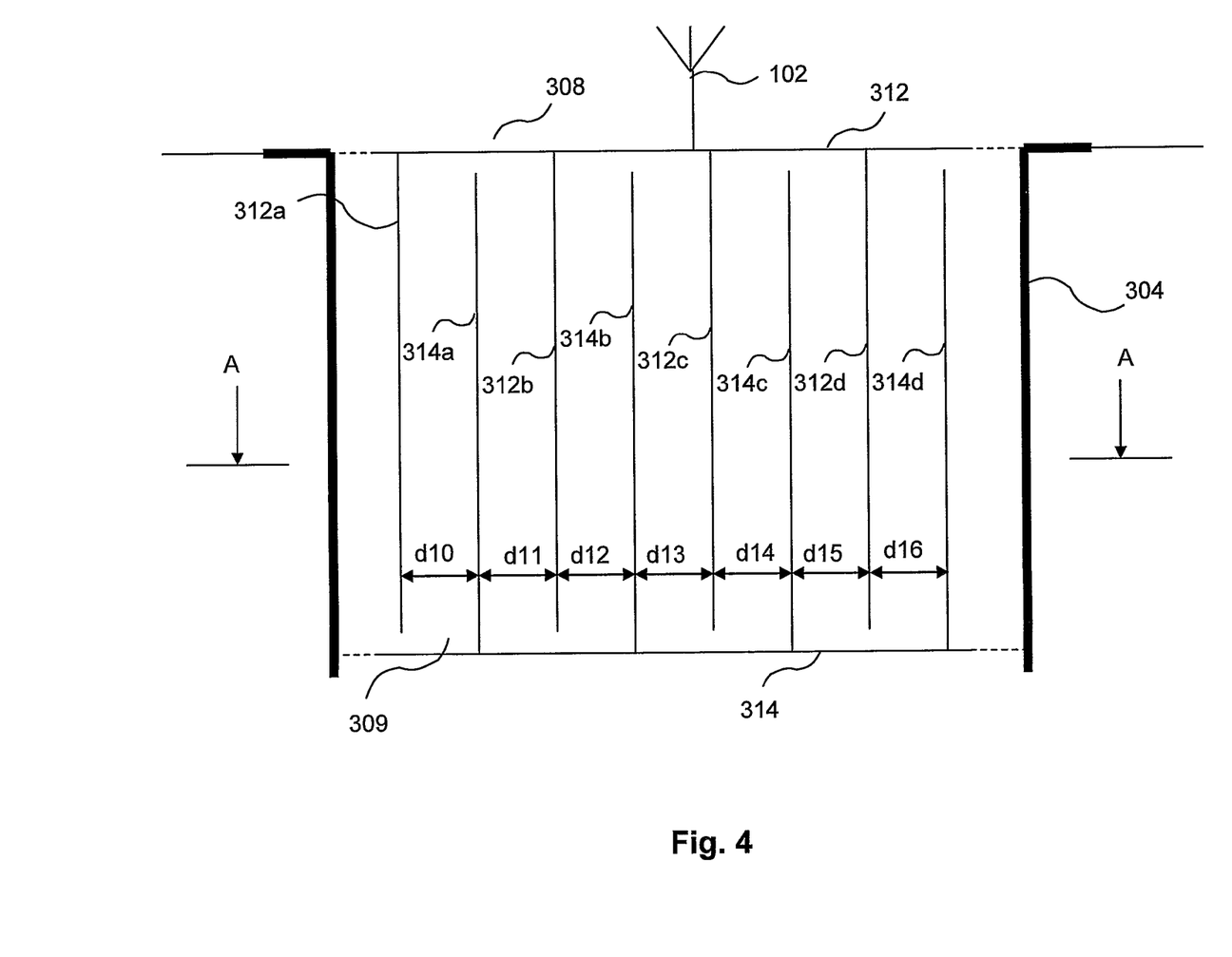
FIG. 4 diagrammatically shows a cross-sectional view of another embodiment of the feedthrough according to the present invention.
Figure 5:
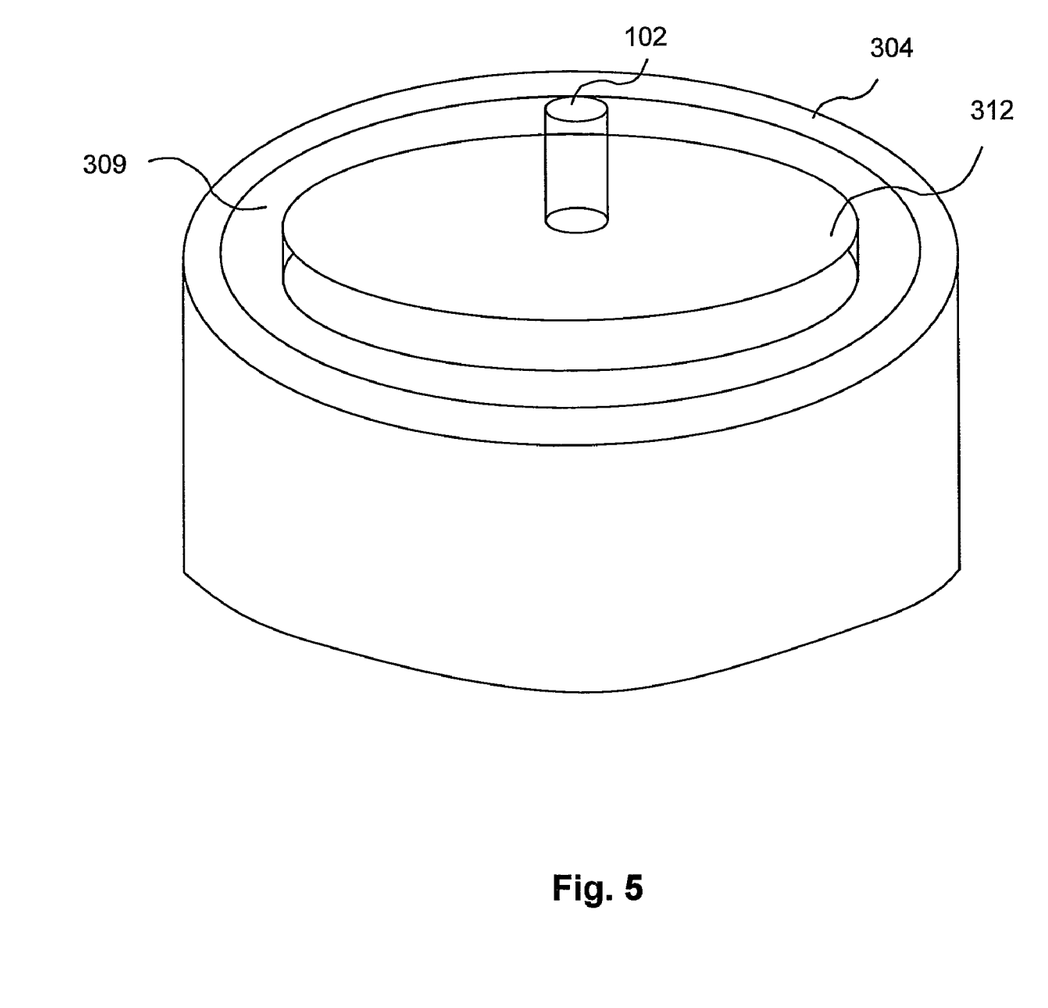
FIG. 5 is a diagrammatic perspective view of the feedthrough shown in FIG. 4.

The antenna 102 is attached to a first connecting element 312. A second connecting element 314 is connected to the RF circuit (se FIG. 1). In this embodiment, the feedthrough housing 304 has a circular cross-section in a plane perpendicular to the plane of the cross-section shown in FIG. 4. The first and second connecting element 312 and 314, respectively, has a circular shape in the plane perpendicular to the plane of the cross-section shown in first and second connecting element 312 and 314, respectively. FIG. 4, and, thus, a cylindrical cavity 309 is formed by the housing 304 and the In FIG. 5, the housing 304 and the first connecting element 312 are shown in a top perspective view. A lower part of the antenna 102 is also shown.

Furthermore, the first connecting element 312 is interconnected to at least one first capacitor plate 312a-312d, which in this embodiment is four. The capacitor plates 312a-312d are arranged within the cavity 309. In this embodiment, this first set of plates 312a-312d function as anode plates. In the same manner, as illustrated, second connecting element 314 is interconnected to a number of at least one second capacitor plate 314a-314d, which in this embodiment is four. The second set of capacitor plates 314a-314d are also arranged within the cavity 309. In this embodiment, this second set of plates 314a-314d function as cathode plates. Of course, as the skilled man realizes, the number of capacitor plates can be varied in accordance with, for example, requirements regarding size or in order to tune the capacitance of the capacitor element 308.

Anode plates 312a-312d and cathode plates 314a-314d are arranged in an alternating manner substantially parallel with each other. The anode plates 312a-312d are attached to the first connecting element 312 such that they are substantially perpendicular to the first connecting element 312. Similarly, the cathode plates 314a-314d are attached to the second connecting element 314 such that they are substantially perpendicular to second connecting element 314. In this embodiment, the capacitor plates 312a-312d and 314-314d are substantially rectangular.

Figure 6:
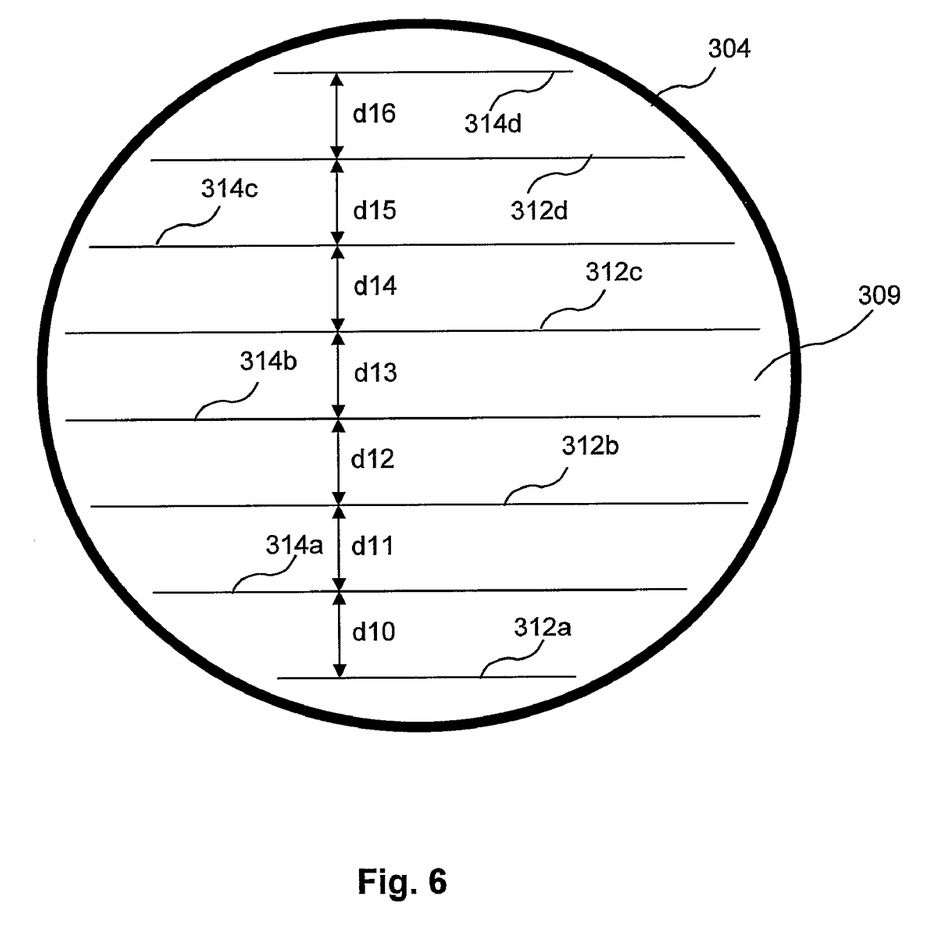
FIG. 6 is a cross-sectional view in plane parallel with the line A-A in FIG. 4 and perpendicular to the view in FIG. 4.
Figure 7:
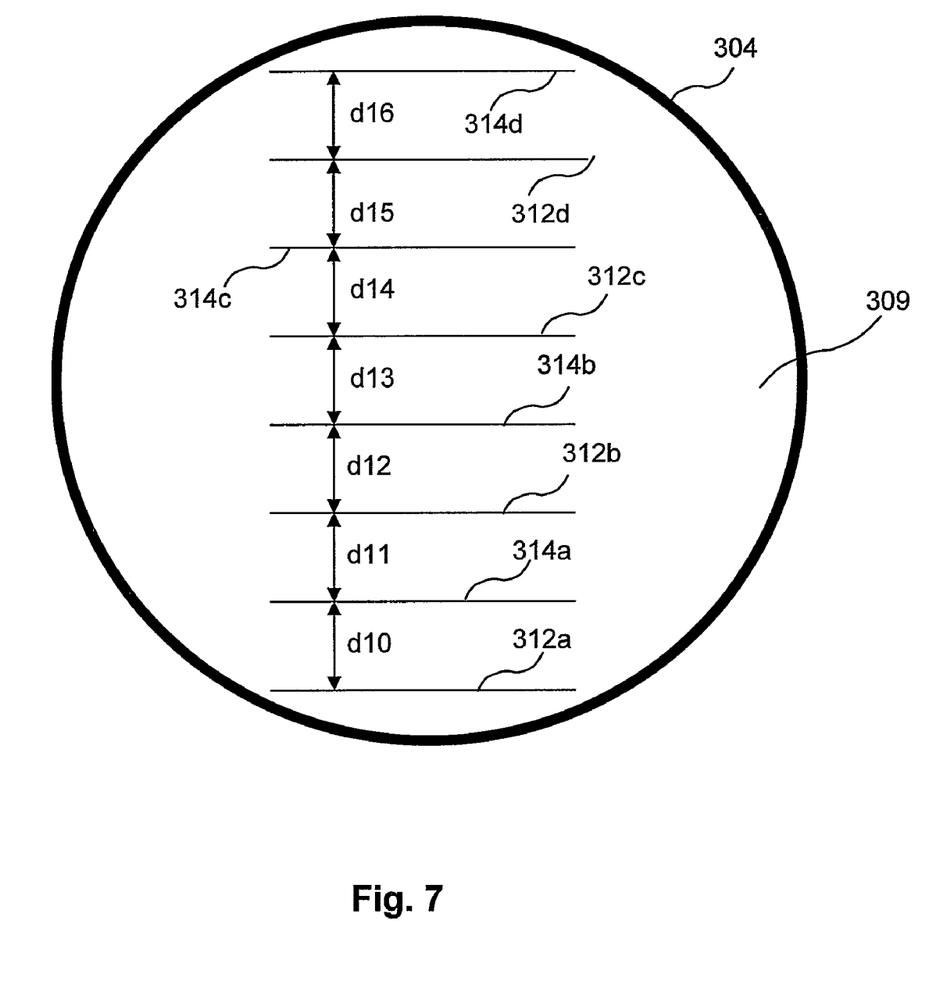
FIG. 7 is a cross-sectional view the plane parallel with the line A-A in FIG. 4 and perpendicular to the view in FIG. 4 of an alternative embodiment to the embodiment shown in FIG. 6.

In FIG. 6 a cross-sectional view in a plane parallel with the line A-A in FIG. 4 is illustrated. As in can be seen in FIG. 6, the widths of adjacent plates differ in this embodiment such that they are gradually becoming wider in order to adapt to the circular shape of the feedthrough housing 304. The lengths of the plates are substantially equal. An alternative embodiment of the present invention is shown in FIG. 7, where the capacitor plates 312a-312d and 314a-314d have a substantially equal widths. Adjacent plates are separated with gaps d10-d16, which in these embodiments are substantially equal i.e. d10=d11=d12=d13=d14=d15=d16 . These gaps d10-d16 may be changed in order to tune the capacitance of the capacitor element 308.

The inner cavity 309 defined by the feedthrough housing 304 and including the intermediate plates 312a-312d and 314a-314d is filled with an isolating dielectric material in accordance with the discussion above such that the feedthrough housing 304, the capacitor plates and the isolating dielectric material forms a galvanic isolation and a hermetic seal.

As can be seen from FIGS. 4-7, the capacitor plates 312a-312d, and 314a-314d according to this embodiment have a substantially rectangular shape, see in particular FIGS. 4 and 6. However, as the skilled man within the art realizes, the size and shape of the feedthrough housing 304 can be changed and, hence, the size and shape of the plates, for example, the shape of the intermediate plates may be substantially octagonal or square. In addition, the distances d10-d16 between adjacent plates can vary. As an example, the distances d10, d12, d14, and d16 can be longer than the distances d11, d13, d15, or in other words, d10=d12=d14=d16>d11=d13=d15.

As discussed above, the capacitor element 308 is preferably dimensioned to withstand a voltage exceeding 100 V, and, more preferably, to withstand a voltage in the range of 75-1000 V. Furthermore, the capacitor element 308 is preferably arranged such that the shunt capacitance of the capacitor is minimized.

Figure 8:
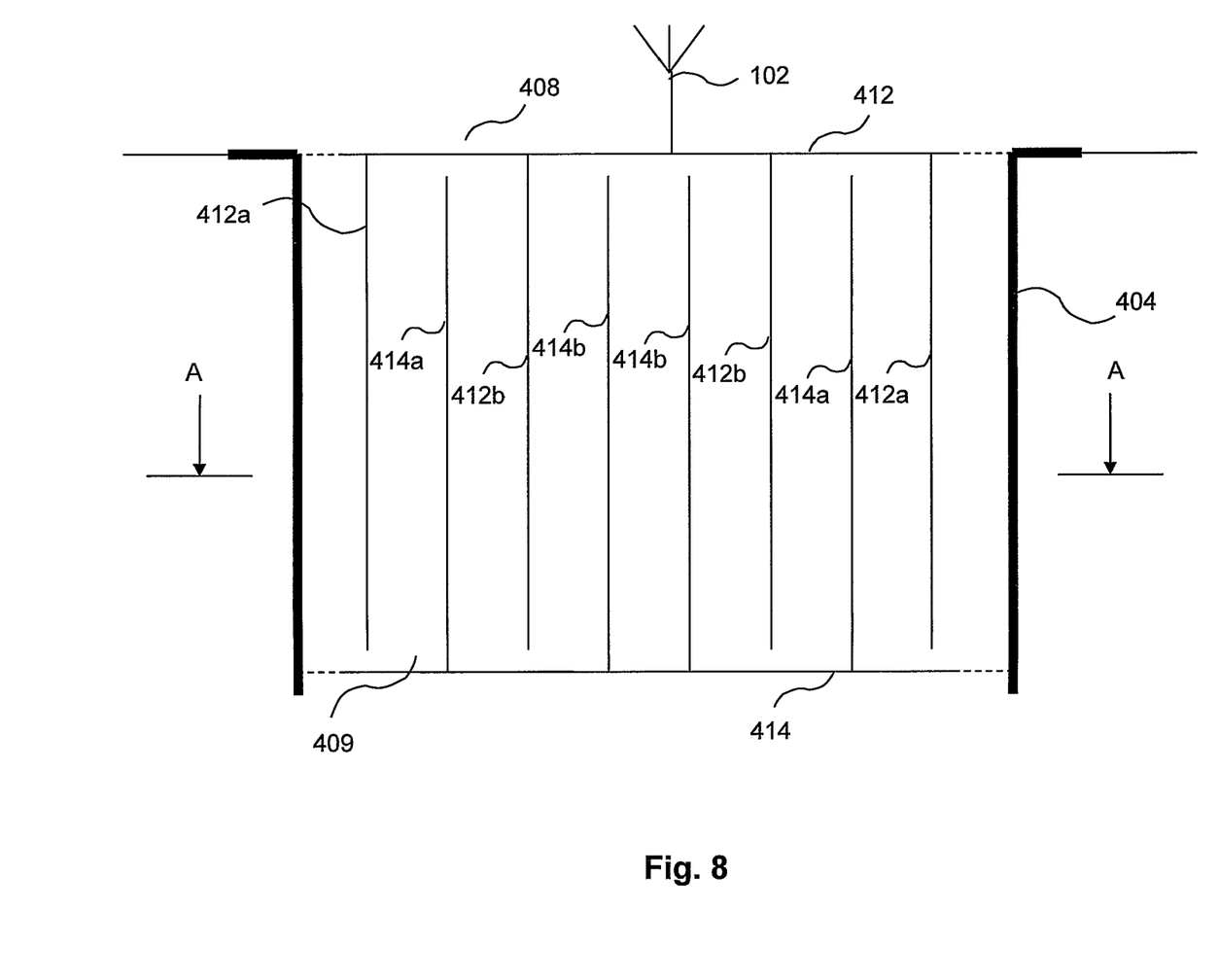
FIG. 8 diagrammatically shows a cross-sectional view of yet another embodiment of the feedthrough according to the present invention.
Figure 9:
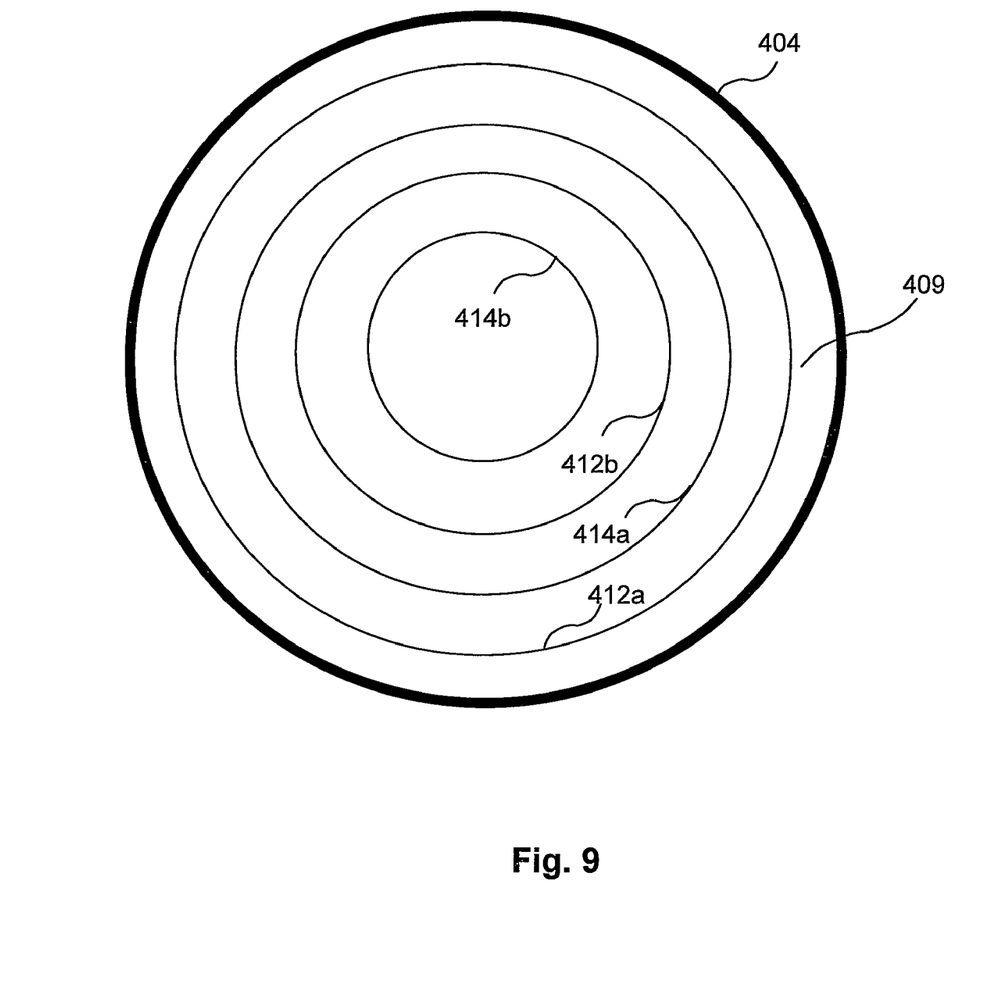
FIG. 9 is a cross-sectional view in plane parallel with the line A-A in FIG. 8 and perpendicular to the view in FIG. 8.

With reference now to FIGS. 8 and 9, another embodiment of the feedtrough including a capacitor according to the present invention will be described. Like or similar parts having like or similar function shown in FIGS. 1 and 2, respectively, are denoted with the same reference numerals. The feedthrough includes a capacitor element 408 and a feedthrough housing 404. As described above, the capacitor body or capacitor element 408 functions both as a hermetic seal and galvanic isolation and, hence, size, cost, and possible interference leakage can be reduced.

The antenna 102 is attached to a first connecting element 412. A second connecting element 414 is connected to the RF circuit (se FIG. 1). Preferably, the first connecting element 412 and the second connecting element 414 are arranged in the feedthrough housing 404 such that an inner cavity 409 is defined. In this embodiment, the feedthrough housing 404 has a circular cross-section in a plane parallel with the line A-A in FIG. 8. The first and second connecting elements 412 and 414, respectively, have a circular shape in the plane perpendicular to the plane parallel with the line A-A in FIG. 8, and, thus, a cylindrical cavity 409 is formed by the housing 404 and the first and second connecting elements 412 and 414, respectively.

Furthermore, the first connecting element 412 is interconnected to at least one first capacitor plate 412a-412b, which in this embodiment is two. The capacitor plates 412a-412b are arranged within the cavity 409. According to this embodiment, the at least one first capacitor plate 412a-412b function as anode plates. In the same manner, as illustrated, the second connecting element 414 is interconnected to at least one second capacitor plate 414a-414b, which in this embodiment is two. The capacitor plates 414a-414b are also arranged within the cavity 409. In this embodiment, the at least one second capacitor plate 41a-414b function as cathode plates. Of course, as the skilled man realizes, the number of intermediate plates can be varied in accordance with, for example, requirements regarding size or in order to tune the capacitance of the capacitor element 408.

Anode plates 412a-412b and cathode plates 414a-414b are arranged in an alternating manner as substantially concentric cylinders. The anode plates 412a-412b are attached to the first connecting element 412 such that they are substantially perpendicular to first connecting element 412. Similarly, the cathode plates 414a-414b are attached to second connecting element 414 such that they are substantially perpendicular to second connecting element 414.

In FIG. 9 a cross-sectional view in a plane parallel with the line A-A in FIG. 8 is illustrated. As in can be seen in FIG. 9, the capacitor plates 412a-412b and 414a-414b are arranged in a substantially concentric manner.

The inner cavity 409 defined by the feedthrough housing 404 including the capacitor plates 412a-412b and 414a-414b is filled with an isolating dielectric material in accordance with the discussion above such that the feedthrough housing 404, the capacitor plates and the isolating dielectric material forms a galvanic isolation and a hermetic seal.

As discussed above, the capacitor element 408 is preferably dimensioned to withstand a voltage exceeding 100 V, and, more preferably, to withstand a voltage in the range of 75-1000 V. Furthermore, the capacitor element 408 is preferably arranged such that the shunt capacitance of the capacitor is minimized.

Figure 10:
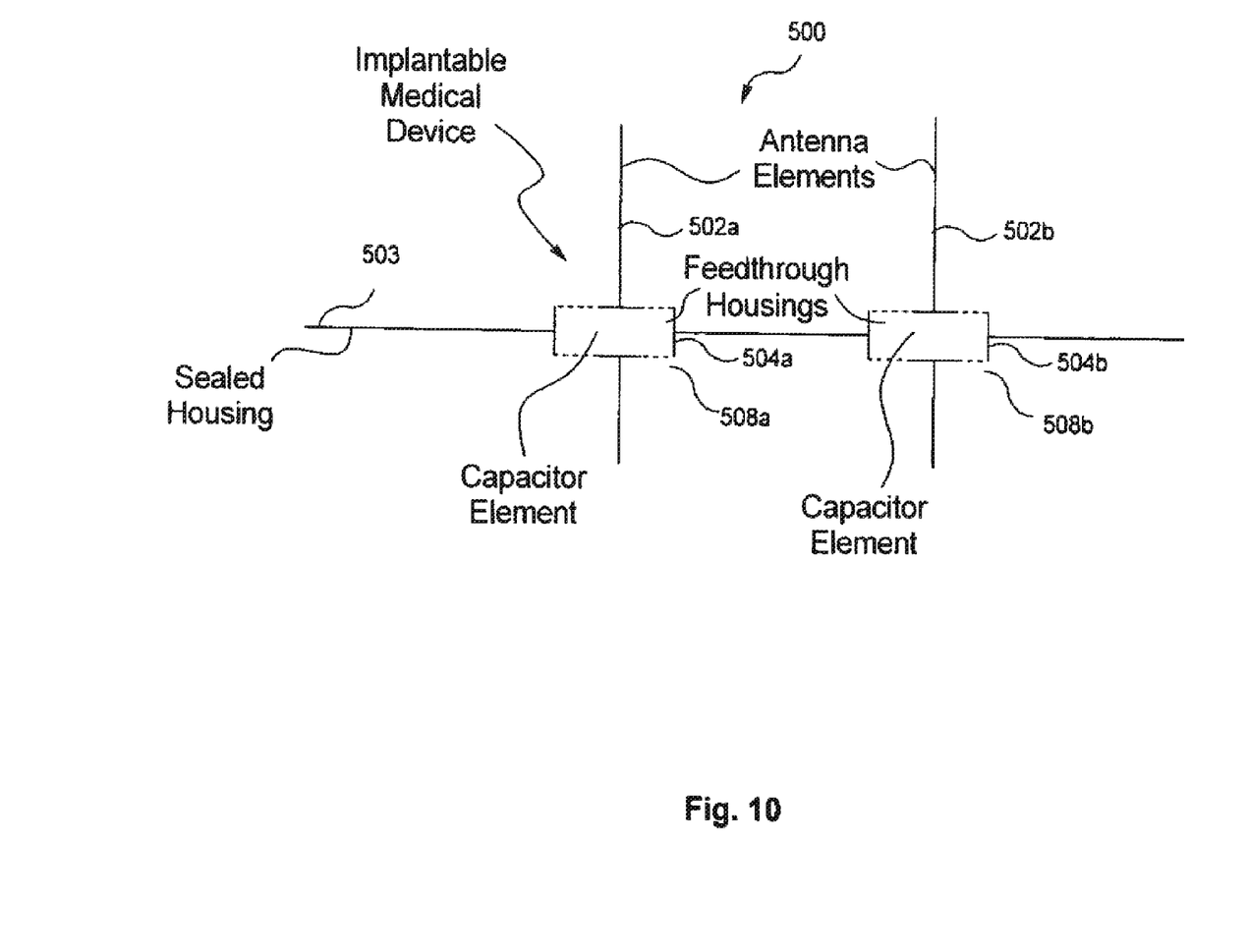
FIG. 10 diagrammatically shows a cross-sectional view of still another embodiment of the feedthrough according to the present invention.

Turning now to FIG. 10, a further embodiment of the present invention will be described. In this embodiment, the implantable device 500 has a balanced antenna, for example, a dipole antenna, including first and second antenna elements 502a, 502b, respectively. The antenna elements 502a, 502b, are arranged in first and second feedthroughs, respectively, which feedthroughs, in turn, are arranged in a hermetically sealed housing 503 of the implantable device 500. Each feedthrough includes a capacitor element 508a, 508b and a feedthrough housing 504a, 504b. As described above, each one of the capacitor bodies or capacitor elements 508a and 508b functions both as a hermetic seal and galvanic isolation and, hence, size, cost, and possible interference leakage can be reduced. Furthermore, the capacitor elements 508a and 508b are preferably dimensioned to withstand a voltage exceeding 100 V, and, more preferably, to withstand a voltage in the range of 75-1000 V. In addition, the capacitor elements 508a and 508b are arranged such that the shunt capacitance of the capacitor is minimized. The capacitor elements 508a and 508b may each have a design in accordance with any one of the embodiments discussed herein with reference to FIGS. 1-9.

In yet another embodiment, the balanced antenna, for example, a dipole antenna, including a first and a second antenna element is arranged in a single feedthrough. In this case, the feedthrough contains two capacitor elements, one for respective antenna element, separated from each other with an electrically isolating element. As described above, each one of the capacitor bodies or capacitor elements functions both as a hermetic seal and galvanic isolation and, hence, size, cost, and possible interference leakage can be reduced. Furthermore, the capacitor elements are preferably dimensioned to withstand a voltage exceeding 100 V, and, more preferably, to withstand a voltage in the range of 75-1000 V. Preferably, the capacitor elements 508a and 508b are arranged such that the shunt capacitance of the capacitor is minimized. The capacitor elements may each have a design in accordance with any one of the embodiments discussed herein with reference to FIGS. 1-9.

According to still another embodiment, the antenna is arranged for communication in two frequency bands. For example, the antenna can be arranged for RF-telemetry communication in a first frequency band at 400 MHz and a second frequency band at 2.45 GHz, wherein the first band is used for communication of data such as various operating parameters and physiological data and the second band is used for wake-up signals. The antenna is located through an antenna feedhtrough according to the present invention, for example, the embodiments shown in FIGS. 2-7. It should be noted that the housing effectively is a part of the antenna and affects the radiation properties of the antenna. The housing is further in contact with the tissue. Preferably, the feedthrough or capacitor is dimensioned to constitute a part of the antenna matching at the first frequency band and the second frequency band, respectively.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting example thereof and that the scope of protection is defined by the appended patent claims.

I claim as my invention:

1. An implantable medical device comprising:
a hermetically sealed housing configured for implantation in a subject;
an RF telemetry antenna carried by said housing;
an RF telemetry circuit comprising an RF transmitter and receiver connected to said RF antenna via a conductive path;
a control circuit connected to said RF telemetry circuit that operates said RF telemetry circuit to transmit and receive signals via said RF antenna;
at least one of said RF telemetry circuit and said control circuit comprising an electrical component that is susceptible to damage or operational modification due to interaction with a voltage pulse having a voltage amplitude; and
a feedthrough in said hermetically sealed housing for said conductive path, said feedthrough comprising a feedthrough housing and a capacitor element in said feedthrough housing, said capacitor element being connected in series with said RF telemetry circuit and said RF antenna, and said capacitor element comprising a first capacitor plate configuration connected in series with said RF antenna and a second capacitor plate configuration connected in series with said RF telemetry circuit, said capacitor element being dimensioned to block said voltage amplitude of said pulse.

2. An implantable medical device as claimed in claim 1 wherein said capacitor element forms a matching element for said RF antenna.

3. An implantable medical device as claimed in claim 1 wherein said first capacitor plate configuration faces outwardly relative to said hermetically sealed housing, and is comprised of a bio-compatible material.

4. An implantable medical device as claimed in claim 1 wherein said capacitor element is dimensioned to withstand a voltage, as said voltage amplitude, exceeding 100 V.

5. An implantable medical device as claimed in claim 1 wherein said first capacitor plate configuration comprises a first set of capacitor plates interacted with each other and wherein said second capacitor plate configuration comprises a second set of capacitor plates connected with each other, the respective plates in said first set alternating with respective plates in said second set with adjacent plates being separated by an isolating dielectric material.

6. An implantable medical device as claimed in claim 5 wherein said feedthrough housing has a substantially cylindrical shape and wherein the respective plates of said first set and the respective plates of said second set are substantially circular, and are arranged substantially coaxially in said feedthrough housing.

7. An implantable medical device as claimed in claim 6 wherein each of said first set of capacitor plates and said second set of capacitor plates comprises end plates with intermediate plates therebetween, each of said intermediate plates having a via hole therein, with all capacitor plates in said first set being electrically connected with each other by first conductors that proceed through the respective via holes of the intermediate plates of the second set, and all capacitor plates in said second set being electrically connected with each other by second conductors that proceed through the respective via holes in the intermediate plates of the first set.

8. An implantable medical device as claimed in claim 5 comprising a first connecting element connected to said RF antenna and a second connecting element connected to said RF telemetry circuit, with the plates of said first set being connected to said first connecting element and said plates of said second set being connected to said second connecting element, said plates of said first set being substantially perpendicular to said first connecting element and said plates of said second set being substantially perpendicular to said second connecting element.

9. An implantable medical device as claimed in claim 8 wherein said feedthrough housing has a substantially cylindrical shape, and wherein the respective plates of each of said first and second sets of capacitor plates are substantially rectangular, each plate in each of said first and second sets having a width substantially equal to an inner width of a longitudinal cross-section of said substantially cylindrical feedthrough housing.

10. An implantable medical device as claimed in claim 8 wherein the respective plates of said first and second sets are arranged in substantially concentric cylinders.

11. An implantable medical device as claimed in claim 5 wherein the respective plates of said first and second sets are arranged with substantially equal distances between each other.

* * * * *